(12) United States Patent
Farinella (10) Patent No.: US 12,276,534 B2
(45) Date of Patent: Apr. 15, 2025

(54) PRIMING VALVE TO INDUCE APPROPRIATE PRESSURE AND FLOW PROFILE AND IMPROVE SENSOR READINESS

(71) Applicant: Becton, Dickinson and Company, Franklin Lakes, NJ (US)

(72) Inventor: Andrew C. Farinella, Oradell, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 96 days.

(21) Appl. No.: 18/127,050

(22) Filed: Mar. 28, 2023

(65) Prior Publication Data

US 2023/0236055 A1    Jul. 27, 2023

Related U.S. Application Data (63) Continuation of application No. 16/833,242, filed on Mar. 27, 2020, now Pat. No. 11,644,356, which is a
(Continued)

(51) Int. Cl.
*A61M 5/00* (2006.01)
*A61M 5/14* (2006.01)
(Continued)

(52) U.S. Cl.
CPC ............ *G01F 15/005* (2013.01); *A61M 5/14* (2013.01); *A61M 5/16886* (2013.01); *A61M 5/172* (2013.01); *A61M 39/24* (2013.01); *F16K 31/12* (2013.01); *G01F 1/662* (2013.01); *A61M 2005/1402* (2013.01);
(Continued)

(58) Field of Classification Search
CPC ..... A61M 2005/1402; A61M 2039/242; F16K 31/12
See application file for complete search history.

(56) References Cited

U.S. PATENT DOCUMENTS

| | | |
|---|---|---|
| 4,299,336 A | 11/1981 | Studer |
| 5,463,906 A | 11/1995 | Spani et al. |
| (Continued) | | |

FOREIGN PATENT DOCUMENTS

| | | |
|---|---|---|
| CN | 102458510 A | 5/2012 |
| CN | 204395066 U | 6/2015 |
| (Continued) | | |

*Primary Examiner* — Laura A Bouchelle
(74) *Attorney, Agent, or Firm* — The Webb Law Firm (57) ABSTRACT

A priming valve includes a fluid flow path, a fluid inlet configured to couple to a fluid outlet of a fluid channel including at least one sensor configured to characterize at least one attribute of a fluid, a fluid outlet, a valve seat, and a connector. The connector engages the valve seat to prevent fluid flow via the fluid flow path. The connector is configured to move relative to the valve seat in response to a threshold pressure within the fluid flow path to allow the fluid to flow via the fluid flow path. A flow sensor subassembly for sensing flow of a fluidic medicament may include a priming valve and at least one sensor of a fluid port configured to characterize at least one attribute of a fluid within an administrable fluid source. A method for readying a fluid sensor may use a priming valve.

8 Claims, 10 Drawing Sheets

Related U.S. Application Data continuation of application No. 16/007,245, filed on Jun. 13, 2018, now Pat. No. 10,641,632.

(60) Provisional application No. 62/521,726, filed on Jun. 19, 2017.

(51) Int. Cl.
| | |
|---|---|
| *A61M 5/168* | (2006.01) |
| *A61M 5/172* | (2006.01) |
| *A61M 39/24* | (2006.01) |
| *F16K 31/12* | (2006.01) |
| *G01F 1/66* | (2022.01) |
| *G01F 15/00* | (2006.01) |

(52) U.S. Cl.
CPC .............. *A61M 2039/242* (2013.01); *A61M 2205/3334* (2013.01); *A61M 2205/3375* (2013.01); *A61M 2205/6072* (2013.01)

(56) References Cited

U.S. PATENT DOCUMENTS

| | | | |
|---|---|---|---|
| 5,733,259 A | 3/1998 | Valcke et al. | |
| 5,853,397 A | 12/1998 | Shemesh et al. | |
| 6,155,463 A | 12/2000 | Dentler | |
| 6,981,960 B2 | 1/2006 | Cho et al. | |
| 7,255,006 B2 | 8/2007 | Spanke et al. | |
| 7,264,885 B2 | 9/2007 | Rosen et al. | |
| 7,560,494 B2 | 7/2009 | Steinbrenner et al. | |
| 7,782,202 B2 | 8/2010 | Downie et al. | |
| 7,976,508 B2 | 7/2011 | Hoag | |
| 8,109,933 B2 * | 2/2012 | Truckai | A61B 17/8836 606/94 |
| 8,210,501 B2 | 7/2012 | Lee | |
| 8,328,082 B1 | 12/2012 | Bochenko et al. | |
| 8,355,753 B2 | 1/2013 | Bochenko et al. | |
| 8,385,972 B2 | 2/2013 | Bochenko et al. | |
| 8,394,053 B2 | 3/2013 | Bochenko et al. | |
| 8,544,344 B2 | 10/2013 | Murakami | |
| 8,606,596 B1 | 12/2013 | Bochenko et al. | |
| 8,702,674 B2 | 4/2014 | Bochenko | |
| 8,714,030 B1 | 5/2014 | Liu et al. | |
| 8,758,305 B2 | 6/2014 | Mcmahon | |
| 8,800,966 B2 | 8/2014 | Cordes | |
| 8,904,878 B2 | 12/2014 | Wiest et al. | |
| 8,945,066 B2 | 2/2015 | Bochenko et al. | |
| 9,039,655 B2 | 5/2015 | Prince et al. | |
| 9,078,809 B2 | 7/2015 | Bochenko et al. | |
| 9,101,534 B2 | 8/2015 | Bochenko | |
| 9,205,198 B2 | 12/2015 | Py | |
| 9,514,131 B1 | 12/2016 | Bochenko et al. | |
| 9,541,431 B2 | 1/2017 | Nakano et al. | |
| 9,615,999 B2 | 4/2017 | Bochenko et al. | |
| 9,737,700 B2 | 8/2017 | Raines | |
| 9,744,298 B2 | 8/2017 | Prince et al. | |
| 9,801,787 B2 | 10/2017 | Py | |
| 9,931,498 B2 | 4/2018 | Bochenko | |
| 10,330,209 B2 | 6/2019 | Weaver | |
| 10,641,632 B2 | 5/2020 | Farinella | |
| 2005/0257714 A1 * | 11/2005 | Constantz | A61L 27/12 604/82 |
| 2007/0034016 A1 | 2/2007 | Maginnis et al. | |
| 2007/0161970 A1 | 7/2007 | Spohn et al. | |
| 2008/0243054 A1 | 10/2008 | Mollstam et al. | |
| 2009/0069743 A1 | 3/2009 | Krishnamoorthy et al. | |
| 2009/0127288 A1 * | 5/2009 | Keller | B01D 46/42 222/1 |
| 2009/0157040 A1 | 6/2009 | Jacobson et al. | |
| 2009/0270844 A1 | 10/2009 | Seeley et al. | |
| 2010/0022953 A1 | 1/2010 | Bochenko et al. | |
| 2010/0022987 A1 | 1/2010 | Bochenko et al. | |
| 2010/0063765 A1 | 3/2010 | Carlisle et al. | |
| 2010/0076370 A1 | 3/2010 | Howlett et al. | |
| 2010/0204659 A1 | 8/2010 | Bochenko et al. | |
| 2011/0111794 A1 | 5/2011 | Bochenko et al. | |
| 2011/0112473 A1 | 5/2011 | Bochenko et al. | |
| 2011/0112474 A1 | 5/2011 | Bochenko et al. | |
| 2011/0264069 A1 | 10/2011 | Bochenko | |
| 2011/0295191 A1 | 12/2011 | Injev | |
| 2012/0037266 A1 | 2/2012 | Bochenko | |
| 2012/0323208 A1 | 12/2012 | Bochenko et al. | |
| 2012/0325330 A1 | 12/2012 | Prince et al. | |
| 2013/0018356 A1 | 1/2013 | Prince et al. | |
| 2013/0204227 A1 | 8/2013 | Bochenko et al. | |
| 2013/0225945 A1 | 8/2013 | Prince et al. | |
| 2014/0033827 A1 | 2/2014 | Satou et al. | |
| 2014/0066880 A1 | 3/2014 | Prince et al. | |
| 2014/0276213 A1 | 9/2014 | Bochenko | |
| 2015/0204705 A1 | 7/2015 | Forster et al. | |
| 2015/0211904 A1 | 7/2015 | Forster | |
| 2015/0223732 A1 | 8/2015 | Prince et al. | |
| 2015/0257977 A1 | 9/2015 | Bochenko et al. | |
| 2015/0305982 A1 | 10/2015 | Bochenko | |
| 2017/0056641 A1 | 3/2017 | Bochenko | |
| 2017/0059376 A1 | 3/2017 | Bochenko | |
| 2017/0065809 A1 | 3/2017 | Bochenko | |
| 2017/0130866 A1 | 5/2017 | Rogalka et al. | |
| 2017/0172849 A1 | 6/2017 | Bochenko et al. | |
| 2017/0312429 A1 | 11/2017 | Prince et al. | |
| 2017/0361017 A1 | 12/2017 | Verma et al. | |
| 2018/0085532 A1 | 3/2018 | Desborough et al. | |
| 2018/0089395 A1 | 3/2018 | Desborough et al. | |
| 2018/0345001 A1 | 12/2018 | Heaton et al. | |

FOREIGN PATENT DOCUMENTS

| | | |
|---|---|---|
| CN | 106170653 A | 11/2016 |
| CN | 106769724 A | 5/2017 |
| DE | 4137837 C1 | 10/1992 |
| DE | 102008055167 A1 | 7/2010 |
| EP | 0897102 A1 | 2/1999 |
| EP | 2135630 A1 | 12/2009 |
| EP | 2857803 A1 | 4/2015 |
| JP | 2012525947 A | 10/2012 |
| WO | 0209795 A2 | 2/2002 |
| WO | 2010132290 A2 | 11/2010 |
| WO | 2011126485 A1 | 10/2011 |
| WO | 2011126895 A2 | 10/2011 |
| WO | 2012126744 A1 | 9/2012 |
| WO | 2014016315 A1 | 1/2014 |
| WO | 2014016316 A1 | 1/2014 |
| WO | 2014085395 A1 | 6/2014 |
| WO | 2017040211 A1 | 3/2017 |

* cited by examiner

PRIMING VALVE TO INDUCE APPROPRIATE PRESSURE AND FLOW PROFILE AND IMPROVE SENSOR READINESS

CROSS-REFERENCE TO RELATED APPLICATION

The present application is a continuation of U.S. patent application Ser. No. 16/833,242, entitled "Priming Valve to Induce Appropriate Pressure and Flow Profile and Improve Sensor Readiness", filed Mar. 27, 2020, which is a continuation of U.S. patent application Ser. No. 16/007,245, entitled "Priming Valve to Induce Appropriate Pressure and Flow Profile and Improve Sensor Readiness", filed Jun. 13, 2018 (now U.S. Pat. No. 10,641,632), which claims priority to U.S. Provisional Application Ser. No. 62/521,726, entitled "Priming Valve to Induce Appropriate Pressure and Flow Profile and Improve Sensor Readiness", filed Jun. 19, 2017, the entire disclosures of each of which are hereby incorporated by reference.

BACKGROUND OF THE INVENTION

1. Field of the Disclosure

The present disclosure relates generally to a flow sensor system. More particularly, the present disclosure relates to a flow sensor system and a method of readying a flow sensor of the flow sensor system for characterizing at least one attribute of a fluid to be detected by the flow sensor.

2. Description of the Related Art

There is a need to improve volume accuracy in a bolus delivery using a medical device. It would be advantageous to provide a flow sensor system having a flow sensor with improved flow measurement characteristics.

SUMMARY OF THE INVENTION

The present disclosure provides a system for sensing a flow of a fluidic medicament. The system includes an intelligent injection port which may attach to an injection site (such as a "Y Site" or a stop cock) for manually administered IV injections. The system includes two main sub-assemblies: a single-use flow sensor and a reusable base unit, which fit together prior to use. The single-use flow sensor includes a flow tube sub-assembly.

In accordance with an example of the present invention, priming valve for a fluid sensor associated with a medical device may include a valve comprising a fluid flow path, a fluid inlet at a first end of the fluid flow path configured to couple to a fluid outlet of a fluid channel including at least one sensor configured to characterize at least one attribute of a fluid, a fluid outlet at a second end of the fluid flow path, a valve seat, and a connector that engages the valve seat to prevent fluid flow between the fluid inlet and the fluid outlet via the fluid flow path, wherein the connector is configured to move relative to the valve seat in response to a threshold pressure within the fluid flow path to allow the fluid to flow between the fluid inlet and the fluid outlet of the valve via the fluid flow path.

According to further examples, the threshold pressure is 5-50 psi.

According to further examples, the connector comprises a sidewall extending between an inlet end and an outlet end of the connector, wherein the valve seat comprises a sidewall extending between an inlet end and an outlet end of the valve seat, and wherein at least a portion of the valve seat extends within the connector such that an inner surface of the sidewall of the connector faces an outer surface of the sidewall of the valve seat.

According to further examples, the outer surface of the sidewall of the valve seat comprises a lip portion that extends radially outward from the sidewall of the valve seat, and wherein the inner surface of the sidewall of the connector is slidingly and sealingly engaged with the lip portion of the valve seat.

According to further examples, the lip portion of the valve seat comprises one of a molded lip seal and an o-ring.

According to further examples, an inner surface of the sidewall of the valve seat defines a first portion of the fluid flow path extending from the fluid inlet of the valve to at least one opening in the sidewall of the valve seat, wherein the at least one opening in the sidewall of the valve seat is located in a direction toward the fluid outlet of the valve with respect to the lip portion of the valve seat, and wherein the inner surface of the sidewall of the connector and the outer surface of the sidewall of the valve seat define a second portion of the fluid flow path extending from the opening toward the fluid outlet of the valve.

According to further examples, the connector is configured to move axially away from the inlet end of the valve seat in a direction toward the outlet end of the valve seat in response to the threshold pressure within the fluid flow path to allow the fluid to flow between the fluid inlet and the fluid outlet of the valve.

According to further examples, a portion of the sidewall of the connector extends radially inward at the inlet end of the connector.

According to further examples, the outer surface of the sidewall of the valve seat comprises at least one abutment surface that extends radially outward from the sidewall of the valve seat, wherein the at least one abutment surface is configured to engage the portion of the sidewall of the connector that extends radially inward to inhibit further movement of the connector axially away from the inlet end of the valve seat in the direction toward the outlet end of the valve seat.

According to further examples, the inner surface of the sidewall of the connector comprises at least one detent extending radially inward from the sidewall.

According to further examples, the outer surface of the sidewall of the valve seat comprises at least one abutment surface extending radially outward from the sidewall, wherein the at least one abutment surface is configured to engage the at least one detent to inhibit further movement of the connector axially away from the inlet end of the valve seat in the direction toward the outlet end of the valve seat.

According to further examples, the outer surface of the sidewall of the valve seat comprises at least one additional abutment surface extending radially outward from the sidewall, wherein the at least one additional abutment surface is located in a direction toward the inlet end of the valve seat with respect to the at least one abutment surface, and wherein the at least one additional abutment surface is configured to engage the at least one detent to inhibit movement of the connector axially toward the inlet end of the valve seat in a direction away from the outlet end of the valve seat.

According to further examples, the valve further comprises an additional fluid flow path between the fluid inlet and the fluid outlet of the valve.

According to further examples, the inner surface of the sidewall of the connector comprises an angled surface that extends radially inward toward the outlet end of the connector, wherein the outer surface of the sidewall of the valve seat comprises a valve seat surface, and wherein the angled surface of the connector engages the valve seat surface of the valve seat to prevent fluid flow between the fluid inlet and the fluid outlet via the fluid flow path.

According to further examples, the valve comprises a connection at the fluid outlet at the second end of the fluid flow path configured to connect to an inlet configured to deliver the fluid from the administrable fluid source to a fluid pathway that provides the fluid to said medical device.

In accordance with an example of the present invention, a flow sensor sub-assembly for sensing flow of a fluidic medicament may include at least one sensor of a fluid port configured to characterize at least one attribute of a fluid within an administrable fluid source, the fluid port comprising: a fluid channel, a fluid inlet at a first end of the fluid channel configured to couple to an outlet of an administrable fluid source, and a fluid outlet at a second end of the fluid channel; and a priming valve attached to the fluid outlet at the second end of the fluid channel, wherein the priming valve is configured to prevent fluid flow from the fluid outlet at the second end of the fluid channel when closed, and wherein the priming valve is configured to open to allow the flow of the fluid from the fluid outlet at the second end of the fluid channel in response a threshold pressure within the fluid channel.

BRIEF DESCRIPTION OF THE DRAWINGS

The above-mentioned and other features and advantages of this disclosure, and the manner of attaining them, will become more apparent and the disclosure itself will be better understood by reference to the following descriptions of examples of the disclosure taken in conjunction with the accompanying drawings, wherein.

Corresponding reference characters indicate corresponding parts throughout the several views. The exemplifications set out herein illustrate exemplary examples of the disclosure, and such exemplifications are not to be construed as limiting the scope of the disclosure in any manner.

DETAILED DESCRIPTION

The following description is provided to enable those skilled in the art to make and use the described examples contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary.

As used in the specification and the claims, the singular form of "a", "an", and "the" include plural referents unless the context clearly dictates otherwise.

As used herein, "proximal" shall refer to a part or direction located away or furthest from a patient (upstream), while distal shall refer to a part or direction towards or located nearest to a patient (downstream). Also, a drug substance is used herein in an illustrative, non-limiting manner to refer to any substance injectable into the body of a patient for any purpose. Reference to a patient may be to any being, human or animal. Reference to a clinician may be to any person or thing giving treatment, e.g., a nurse, doctor, machine intelligence, caregiver, or even self-treatment.

As used herein, the phrase "inherently hydrophobic" refers to a surface that naturally excludes water molecules rather than by a process of drying, such as drying by hot air.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

Unless otherwise indicated, all numbers expressing quantities used in the specification and/or claims are to be understood as modified in all instances by the term "about."

Flow Sensor System

FIGS. 1-4 illustrate an exemplary configuration of a flow sensor system 200 of the present disclosure. Referring to FIGS. 1-4, a flow sensor system 200 of the present disclosure includes two main assemblies which fit together prior to use: a flow sensor 210 and a base 220. In one example, the flow sensor 210 can be a single-use flow sensor which is engageable with a reusable base 220. The flow sensor system 200 is an intelligent injection port. The flow sensor system 200 is attachable to an injection site ("Y Site" or stop cock, for example) for manually administered IV injections.

The flow sensor system 200 of the present disclosure can reduce medication error at bedside during bolus delivery. The flow sensor system 200 of the present disclosure can also provide a record of and electronically measure bolus delivery, which allows monitoring bolus delivery and automatic documentation of bolus delivery as part of a patient's health record. The flow sensor system 200 of the present disclosure can also provide alerts when bolus delivery inconsistent with a patient's medical record is about to occur.

Referring to FIGS. 1-4, in one example, the base 220 is a non-sterile, reusable device that houses a battery, a scanner (either optical, mechanical, inductive, capacitive, proximity, or RFID), electronics, and a wireless transmitter. In some examples, the base 220 is battery powered and rechargeable. In some examples, each base 220 has a unique serial number imprinted on a surface of the base 220 or embedded therein that may be transmitted to a data system before use. The data system can be a local computer or tablet "computer", a cellular phone, another medical device, or a Hospital Data System.

Referring to FIGS. 1-4, in one example, the base 220 is removably connectable to the flow sensor 210 and includes at least one deflectable wing tab 280 defining an opening for receiving at least a portion of the flow sensor 210 therein and for securing the flow sensor 210 within a portion of the base 220 prior to use. In one example, a pair of wing tabs 280 secure the flow sensor 210 within the base 220. The wing tabs 280 may be flexible to the extent that they may be outwardly deflected to allow for passage of the flow sensor 210 therethrough. In one example, the flow sensor 210 is a pre-sterilized disposable device having an injection port 130 and a distal tubing connection, such as a Luer tip 109, which may be optionally covered by a Luer cap 108.

Figure 3:
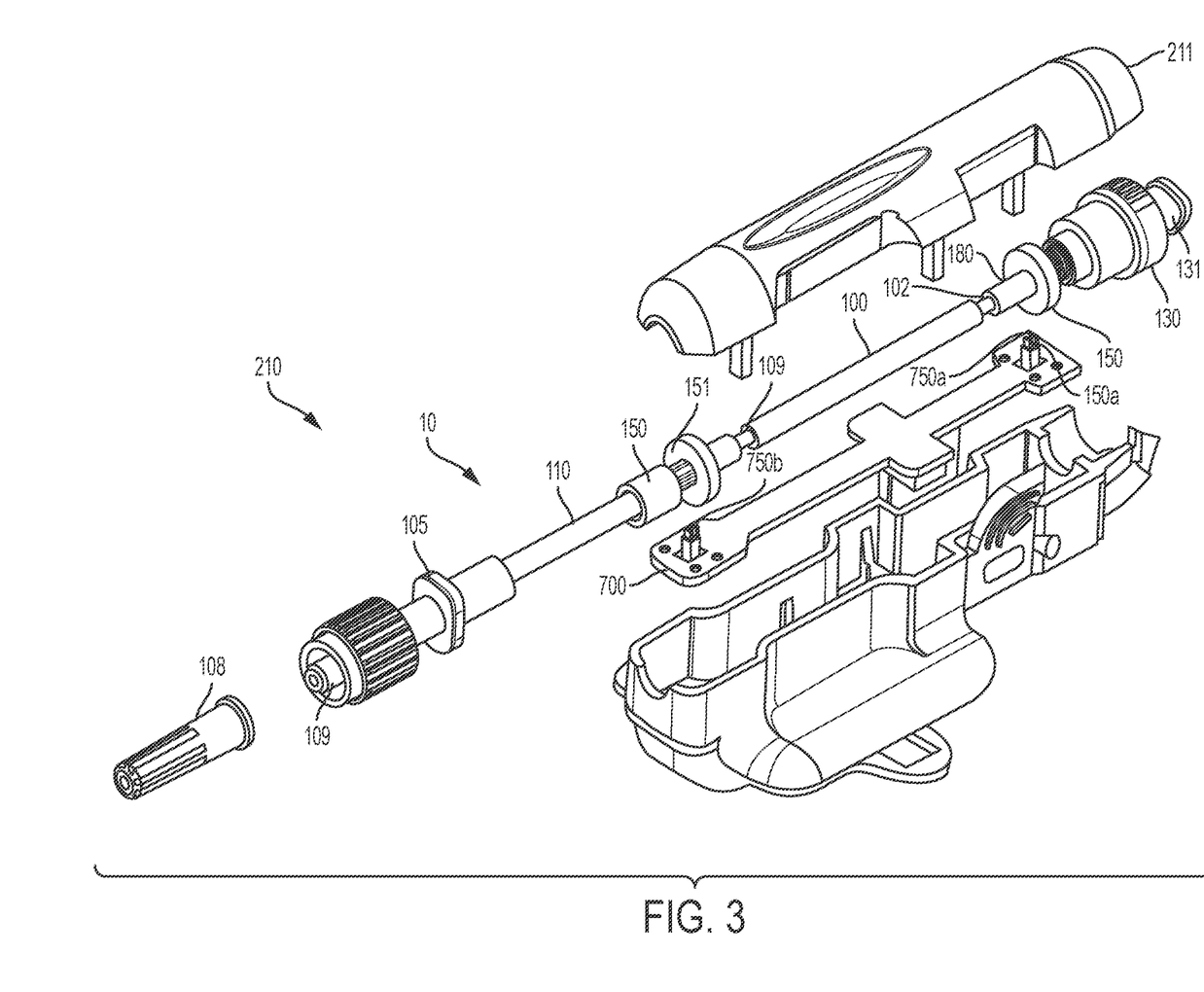
FIG. 3 is an exploded, perspective view of a flow sensor of a flow sensor system in accordance with an example of the present invention.
Figure 4:
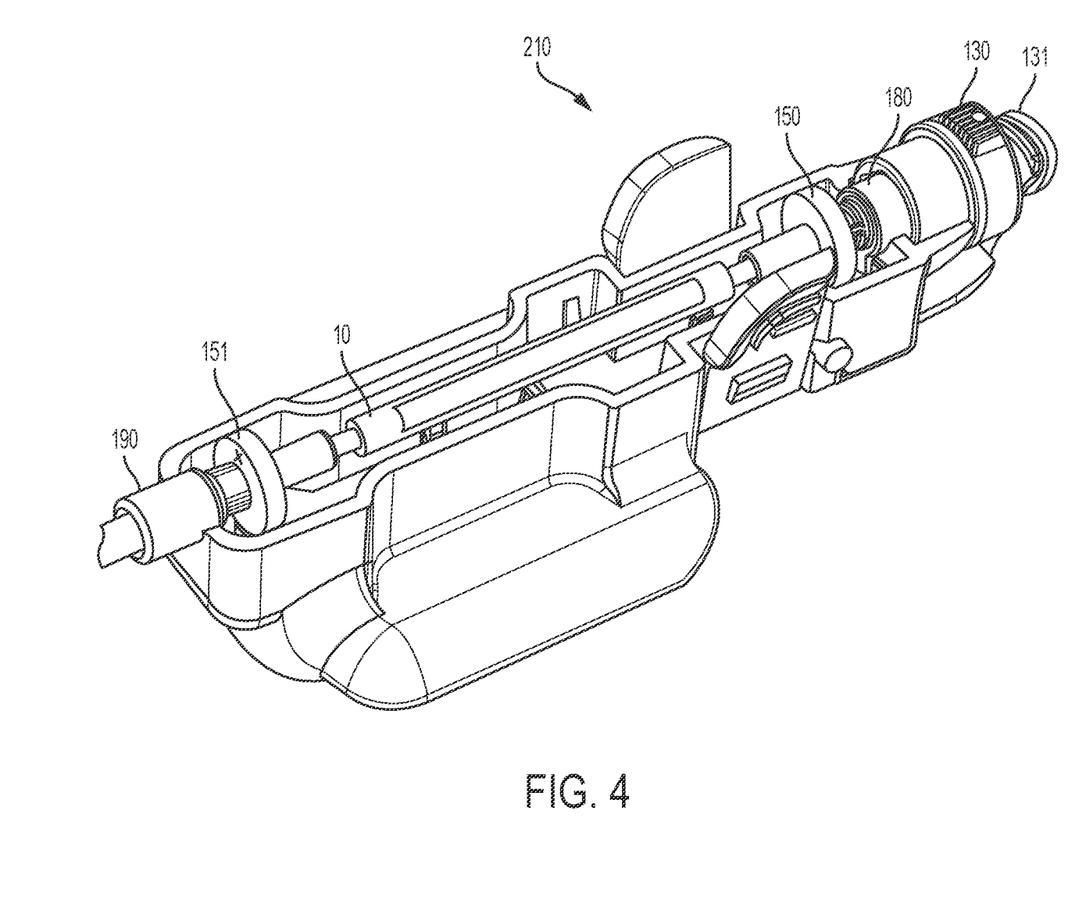
FIG. 4 is a perspective view of a flow sensor of a flow sensor system in accordance with an example of the present invention.

With reference to FIG. 3, the flow sensor 210 may include a flow tube sub-assembly 10 consisting of a flow tube 100 having an outlet end 101 and an inlet end 102. The outlet end 101 may be provided in fluid communication with an outlet tubing 110 having an outlet connection 105 including a Luer tip 109 which may be optionally covered by a flow restrictor, as described herein. In a preferred example, the outlet connection 105 is a plastic connector with a Luer tip 109, however, any suitable method to inject the medicament into a patient is envisaged to be within an aspect of an example of the invention. For example, it may be desirable to replace the outlet connection 105 and tubing 110 with a needle for direct injection/infusion into a patient.

The inlet end 102 may be coupled to the reservoir of a medication pen or infusion reservoir. The inlet end 102 of the flow tube 100 may be provided in fluid communication with an injection port 130, and may optionally include a connection such as a threaded Luer lock 131 which is engageable with a source of a fluid to be injected. A pierceable septum (not shown) may be provided with the injection port 130 for maintaining sterility prior to use. In one example, the flow tube 100 is comprised of a medical grade stainless steel and is approximately 50 mm long with a 1.0 mm inner diameter and a 1.6 mm outer diameter.

In one example, the flow sensor system 200 supports injections using any Luer-lock type syringe or liquid medicament container. Additionally, the flow sensor system 200 is designed to work with encoded syringes that have a special barcode identifier on the Luer collar of the syringe, called "encoding". Preferably, encoded syringes include commercially-available drugs in prefilled syringes with a special barcode that stores information about the medication contained within the syringe. Encoded syringes are ready-to-use, passive, and disposable. The encoding syringes store the drug name and concentration contained within the syringe. Additional characteristics such as drug source, container size, drug manufacturer source, drug category color, among others, may also be included. When an encoded syringe is attached to the injection port 130 of the flow sensor 210, this barcode information is read by a scanner in the base 220 and wirelessly transmitted by the flow sensor system 200 to the data system. Preferably, the 2-D barcodes will be added to syringes during the filling process. The flow sensor system 200 also accommodates syringes not having encoding.

The present disclosure provides a flow sensor sub-assembly for sensing flow of a fluidic medicament. The flow sensor 210 also includes a first piezo element or an upstream transducer 150 and a second piezo element or a downstream transducer 151. The first piezo element 150 may be provided with an inlet fitting 180, as shown in FIG. 3, for coupling with the injection port 130. Similarly, the second piezo element 151 may be provided with an outlet fitting 190, for coupling with the outlet tubing 110. The first and second piezo elements 150 and 151 are configured to transmit an ultrasonic signal therebetween indicative of a flow of the fluidic medicament in the flow tube 100. In an example, the first piezo element 150 and the second piezo element 151 are annular in shape and encircle the flow tube 100 at each respective mounting point.

The flow sensor 210 includes a first spring contact 750*a* and a second spring contact 750*b*. In one example, the spring contacts 750*a*, 750*b* are secured to a base 700 that has a circuit for conducting an electrical signal to and from the spring contacts 750*a*, 750*b* to a microprocessor. The first spring contact 750*a* is in electrical communication with a first piezo element 150 and the second spring contact 750*b* is in electrical communication with a second piezo element 151. The first spring contact 750*a* has a first contact force against the first piezo element 150 and the second spring contact 750*b* has a second contact force against the second piezo element 151. The first contact force may be equivalent to the second contact force. The first and second piezo elements 150, 151 vibrate due to fluid flow through the flow tube 100 of the flow sensor 210. Vibration of the first and second piezo elements 150, 151 creates an ultrasonic signal which can be detected and communicated electronically to the microprocessor. The microprocessor is configured to correlate the ultrasonic signal to a fluid flow rate through the flow tube 100 and provide a fluid flow rate output to the user.

Method of Readying a Flow Sensor

Figure 1:
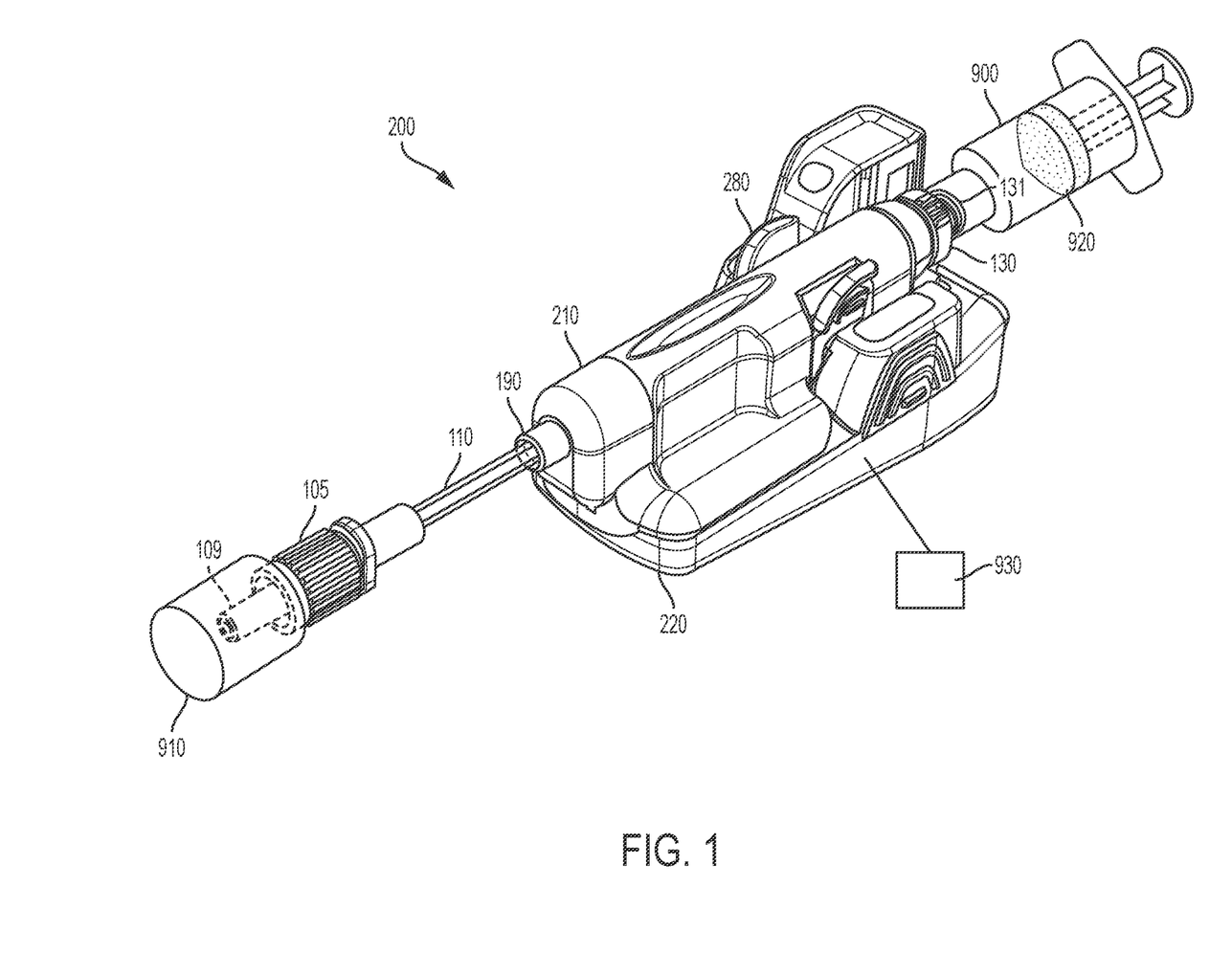
FIG. 1 is a distally-directed perspective view of a flow sensor system in accordance with one example of the present invention.
Figure 2:
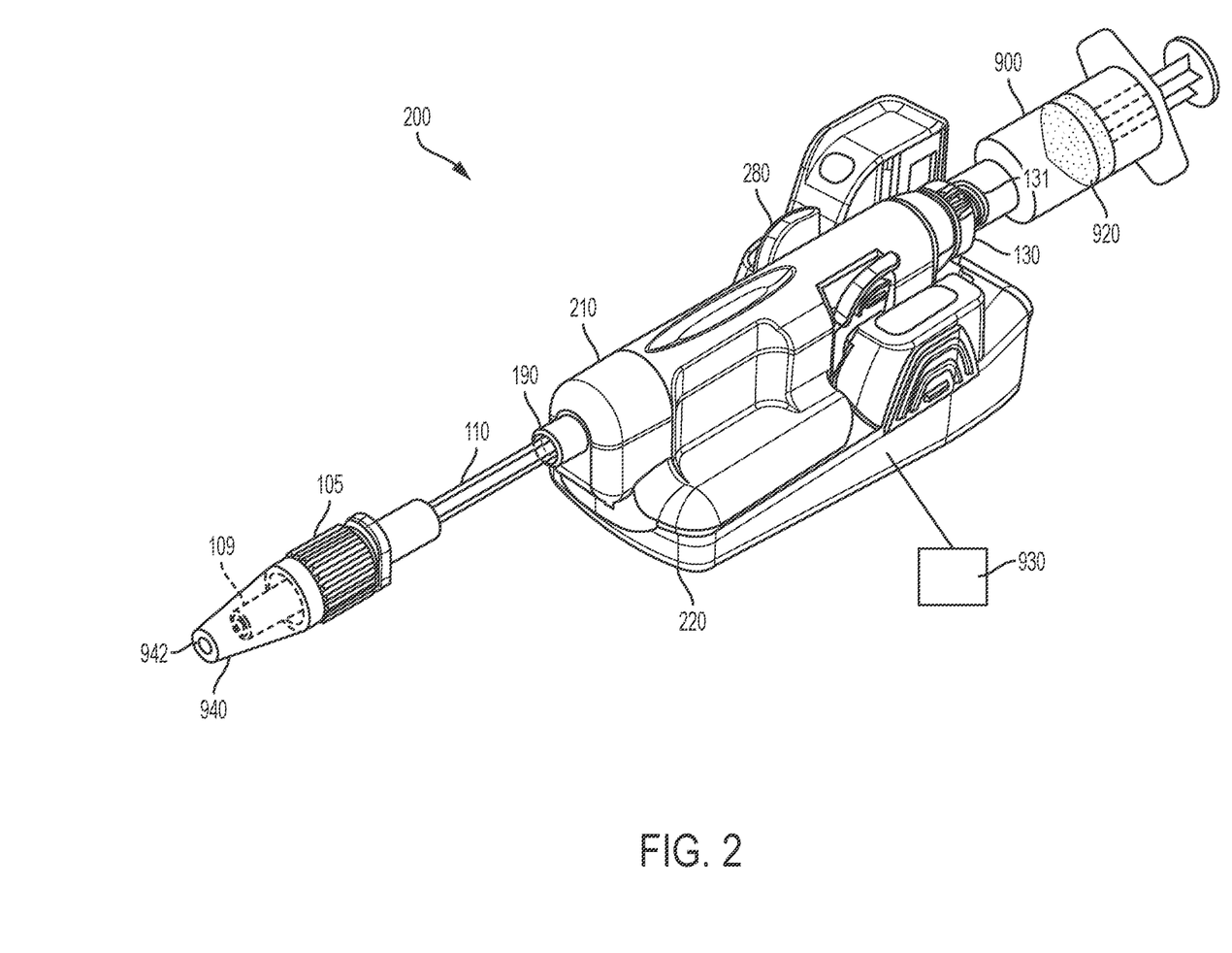
FIG. 2 is a distally-directed perspective view of a flow sensor system in accordance with one example of the present invention.

Referring to FIGS. 1-2, use of a flow sensor system 200 of the present disclosure will now be described. In one example, as the drug is injected, the flow sensor system 200 measures the volume dosed ultrasonically. In order to improve transmission of ultrasonic signals in the flow sensor 210, the present disclosure proposes various examples of increasing a fluid pressure in the flow sensor 210.

During manufacture, flow sensor 210 may be calibrated on a calibration bench. For example, a fluid, such as water, is flowed through the flow sensor 210 to calibrate the ultrasonic signal transmission between the first and second piezo elements 150 and 151. Prior to packaging the flow sensor 210 for shipping, the flow sensor 210 may be dried, such as using hot air, to eliminate any residual fluid that may remain in the flow sensor 210. Without intending to be bound by theory, hot air drying of the fluid path surfaces of the flow sensor 210 contributes to making these fluid path surfaces exhibit their inherently hydrophobic characteristics. In this manner, when the flow sensor 210 is readied for use by priming the flow sensor 210 with a priming fluid, the interior fluid path surface of the flow sensor 210 may not be fully wetted with the priming fluid. Because the flow sensor 210 is configured to generate ultrasonic signals corresponding to a flow rate of the fluid through contact with the internal flow path of the flow sensor 210, the inherently hydrophobic characteristics of the interior surface of the fluid path contribute to a decrease in the ability of the flow sensor 210 to transmit ultrasonic waves. It has been found that wetting the internal surfaces of the flow path through the flow sensor 210, such as by increasing a pressure or maintaining a pressure within the flow path, increases the ultrasonic signal transmission capability of the flow sensor 210.

With reference to FIG. 1, a first method of readying the flow sensor 210 will now be described. In this example, the flow sensor system 200 is prepared for use by attaching the injection port 130 of the flow sensor system 200 to an administrable fluid source, such as a syringe 900 containing a fluid. In some examples, the syringe 900 may contain a priming fluid, such as saline. Prior to connecting the syringe 900, the injection port 130 is desirably cleaned by swabbing the hub according to normal hospital procedure. The syringe 900 can be attached to the injection port 130 by rotating the syringe 900 about its longitudinal axis until the syringe 900 stops, i.e., a secure connection between the syringe 900 and the injection port 130 is made. The syringe 900 has a plunger 920 for delivering the priming fluid from an interior of the syringe 900 when the plunger 920 is pushed in a distal direction.

The outlet connection 105 is capped with a flow restrictor, such as a cap 910. In some examples, the cap 910 is configured to interface with the Luer tip 109 of the outlet connection 105. The cap 910 can be attached to the Luer tip 109 by rotating the cap 910 about its longitudinal axis until the cap 910 stops, i.e., a secure connection between the cap 910 and the Luer tip 109 is made. Once connected to the Luer tip 109, the cap 910 blocks fluid flow from the outlet connection 105.

Next, the plunger 920 of the syringe 900 is pushed in the distal direction to deliver fluid from the syringe 900. Because the cap 910 prevents fluid from flowing out of the outlet connection 105, the priming fluid from the syringe 900 builds fluid pressure within the flow sensor 210. In some examples, the increased fluid pressure of 5-50 psi within the flow sensor 210 can be maintained for a predetermined period of time. For example, the predetermined period of time may be approximately 1-60 seconds.

While the flow sensor 210 is pressurized by the fluid from the syringe 900, at least one first signal is generated by the flow sensor 210 to characterize at least one attribute of fluid. In various examples, the at least one attribute may be fluid flow rate and/or fluid pressure. The manual increase of fluid pressure within the flow sensor 210, while keeping the outlet connection 105 capped, helps eliminate any air between the interior surface of the flow path of the flow sensor 210 and the fluid. In this manner, the interior surface of the flow path of the flow sensor 210 is fully wetted to allow for an increased ultrasonic signal transmission of the flow sensor 210.

Next, the pressure on the plunger 920 of the syringe 900 can be released, and the cap 910 is removed from the Luer tip 109. The outlet connection 105 is attached to an inlet of a fluid pathway (not shown) configured for delivering fluid from an administrable fluid source, such as the syringe 900, to a patient. In some examples, the fluid pathway may be a catheter configured for connecting to a patient. Prior to connecting the fluid pathway to the patient, fluid from the syringe 900 is first expelled from the fluid pathway, such as during the priming of the fluid pathway. As the fluid is delivered from the syringe 900, the fluid flows through the flow sensor 210 and out of the fluid pathway. In some examples, 2-7 ml of fluid may be delivered from the syringe 900 through the fluid pathway. The flow sensor 210 may generate at least one second signal of the same type as the first signal in order to characterize at least one attribute of the fluid. For example, the second signal may characterize the pressure and/or flow rate of fluid through the flow sensor 210. In some examples, the second signal may be increased (i.e., have higher strength) than the first signal due to the internal surfaces of the flow path of the flow sensor 210 being fully wetted. For example, the second signal may be increased over the first signal by 120%, 160%, or 180%, inclusive of the values therebetween. The flow sensor 210 is now primed and ready for use in a fluid delivery procedure.

In various examples, the flow sensor 210 may be in communication with a controller 930. The controller 930 may be configured for receiving information from the flow sensor 210, such as receiving the at least one first signal and the at least one second signal. The controller 930 may be configured to determine that the at least one attribute of the fluid based on the received data from the at least one first signal and the at least one second signal matches at least one condition specified by at least one rule. For example, the controller 930 may be configured for identifying a type of fluid flowing through the flow sensor 210 based on a flow rate of the fluid through the flow sensor 210 for a given fluid pressure at a given fluid temperature. Without intended to be bound by theory, each fluid, such as a fluid medicament, has a unique ultrasonic signature as the fluid flows through the flow sensor 210. The ultrasonic signature may be a function of fluid pressure, temperature, and material composition of the fluid.

In various examples, the controller 930 may generate at least one operation modification signal in response to the characterized at least one attribute matching at least one condition specified by at least one rule. For example, the controller 930 can execute a flow algorithm based on data representing characteristics or attributes of the fluid flow received from the piezo elements 150, 151. In some examples, the syringe 900 may have indicia that, when read by a reading device of the flow sensor system 200 that is in operative communication with the controller 930, causes the controller 930 to initiate a predetermined operating cycle. In some examples, the indicia may be a 2D or 3D barcode, QR code, or any other indicia capable of storing information that, when read by a reading device of the flow sensor system 200, is configured to be interpreted as a set of instructions to be performed by the controller 930. For example, the indicia, when read by the reading device, can cause the controller 930 to initiate a priming cycle for priming the flow sensor 210. In some examples, the priming cycle may comprise generating at least one signal, such as a first signal and a second signal discussed herein.

The controller 930 may transmit, by a transmitter (not shown) the operation modification signal to at least one device. In some embodiments, if a fluid type is determined to be a different type than a desired fluid type, or if a flow rate is determined to be a different flow rate than a desired flow rate, the controller 930 can transmit an operation modification signal to a display and/or a data processing module that causes the module to display an alarm or alert or causes the module to transmit a signal back to the system 200 that stops the fluid flow. The controller 930 can further control the wireless transmitter to transmit injection data representing a type of medication, a dose of a medication, and/or a time of a dose of a medication to the display and/or data processing module. In some embodiments, the controller 930 can automatically transmit the data to the module in response to an automated injection.

Figure 5:
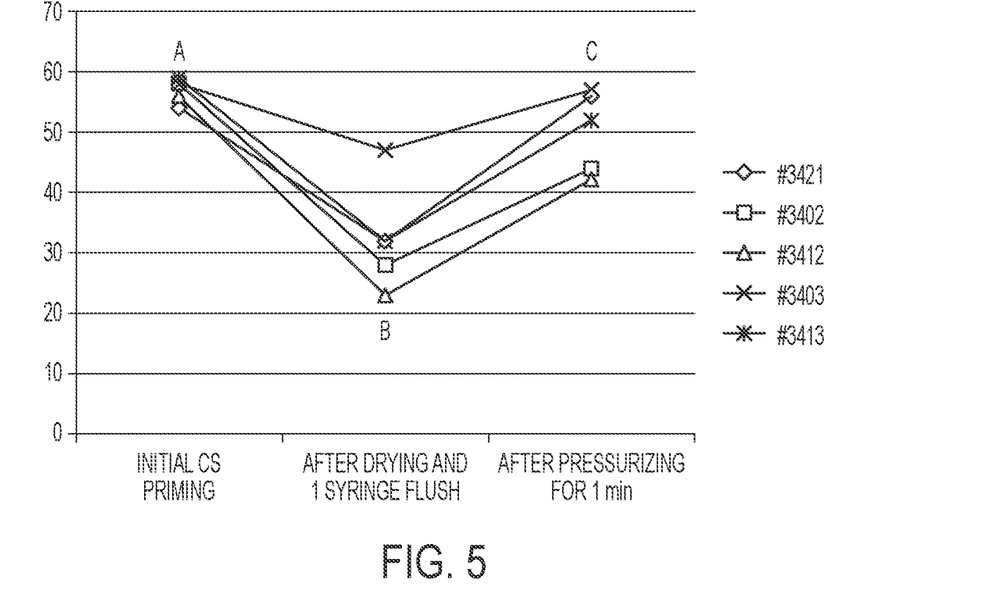
FIG. 5 is a graph showing signal level of a flow sensor of a flow sensor system as a function of time according to one example case.

With reference to FIG. 5, a graph depicting a percentage of signal strength of five flow sensors 210 as a function of time is shown in accordance with one example. Each flow sensor 210 was initially calibrated using a standard calibration routine. The signal readings from each of the flow sensors 210 after calibration are shown as point A on the graph. The flow sensors 210 were then dried with hot air and flushed with a priming fluid without being pressurized. Ultrasonic signal transmission readings were then recorded, shown as point B on the graph. From the graph in FIG. 5, it can be readily observed that signal strength drops for each of the flow sensors 210 after the flow sensors 210 have been dried with hot air. In order to increase the signal level, each flow sensor 210 was capped with a cap 910 and pressurized with a priming fluid, such as saline, for 60 seconds. After the expiration of the pressurization period, another signal reading was taken. Point C in FIG. 5 illustrates that the signal level increases from Point B after the flow sensors 210 have been pressurized with a priming fluid.

With reference to FIG. 2, instead of capping the outlet connection 105 with a cap 910, such as described herein with reference to FIG. 1, the outlet connection 105 may be connected to a vented flow restrictor, such as a vented cap 940. In some examples, the vented cap 940 may be a needle having an inner diameter sufficiently small to be capable of generating back pressure in the flow sensor 210 when fluid is delivered from the syringe 900. For example, the vented cap 940 may be a needle having an outlet of approximately 30 G (0.16 mm ID). In other examples, the vented cap 940 may have an inner diameter of 0.1-0.2 mm. The priming fluid delivered from the syringe 900 builds back pressure within the flow sensor 210. In some examples, the increased fluid pressure of 5-50 psi within the flow sensor 210 can be maintained for a predetermined period of time. For example, the predetermined period of time may be approximately 1-60 seconds.

While the flow sensor 210 is pressurized by the fluid from the syringe 900, at least one first signal is generated by the flow sensor 210 to characterize at least one attribute of fluid. In various examples, the at least one attribute may be fluid flow rate and/or fluid pressure. The manual increase of fluid pressure within the flow sensor 210, while keeping the outlet connection 105 capped, helps eliminate any air between the interior surface of the flow path of the flow sensor 210 and the fluid. In this manner, the interior surface of the flow path of the flow sensor 210 is fully wetted to allow for an increased ultrasonic signal transmission of the flow sensor 210.

Next, the pressure on the plunger 920 of the syringe 900 can be released, and the vented cap 940 is removed from the Luer tip 109. The outlet connection 105 is attached to an inlet of a fluid pathway (not shown) configured for delivering fluid from an administrable fluid source, such as the syringe 900, to a patient. In some examples, the fluid pathway may be a catheter configured for connecting to a patient. Prior to connecting the fluid pathway to the patient, fluid from the syringe 900 is first expelled from the fluid pathway, such as during the priming of the fluid pathway. As the fluid is delivered from the syringe 900, the fluid flows through the flow sensor 210 and out of the fluid pathway. In some examples, 2-7 ml of fluid may be delivered from the syringe 900 through the fluid pathway. The flow sensor 210 may generate at least one second signal of the same type as the first signal in order to characterize at least one attribute of the fluid. For example, the second signal may characterize the pressure and/or flow rate of fluid through the flow sensor 210. In some examples, the second signal may be increased (i.e., have higher strength) than the first signal due to the internal surfaces of the flow path of the flow sensor 210 being fully wetted. For example, the second signal may be increased over the first signal by 120%, 160%, or 180%, inclusive of the values therebetween. The flow sensor 210 is now primed and ready for use in a fluid delivery procedure.

Figure 6:
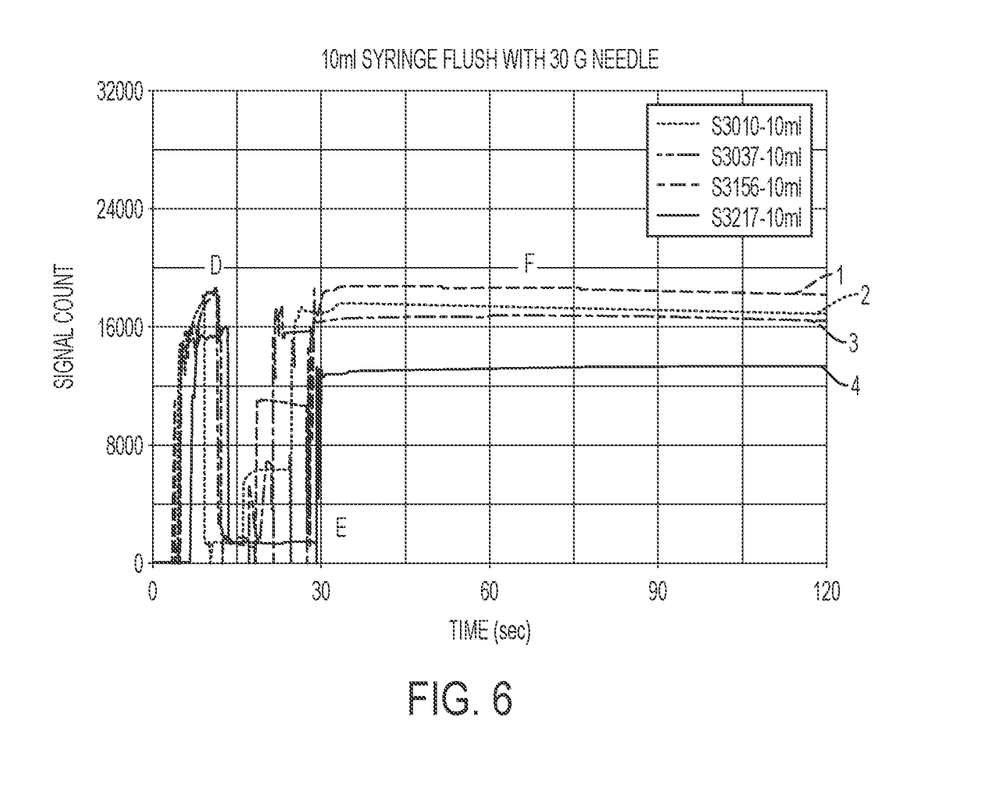
FIG. 6 is a graph showing signal level of a flow sensor of a flow sensor system as a function of time according to another example case.

With reference to FIG. 6, a graph depicting signal level of three flow sensors 210 (labeled 1, 2, 3) as a function of time is shown in accordance with another example. Each flow sensor 210 was provided with a vented cap 940 having a 30 G needle. A signal count was recorded (Point D) during a delivery of 2 ml of fluid from the syringe 900. The vented cap 940 was then removed from each flow sensor 210 and a signal count illustrative of a pressure drop was recorded (Point E). From the graph in FIG. 6, it can be readily observed that signal strength drops for each of the flow sensors 210 after the vented cap 940 is removed from the flow sensors 210. After removing the vented cap 940, 7 ml of fluid was delivered from the syringe 900 through each flow sensor 210. During this step, signal count increased and stabilized at a high value (Point F). A signal level of a fourth flow sensor 210 (labeled 4 in FIG. 6), which has been primed without using the vented cap 940, is shown as a comparative example. The signal strength of the fourth flow sensor 210 is significantly lower than a signal strength of flow sensors 210 that were readied using the vented cap 940 in a manner described herein with reference to FIG. 2.

Flow Sensor System Relief Valve

Figure 7:
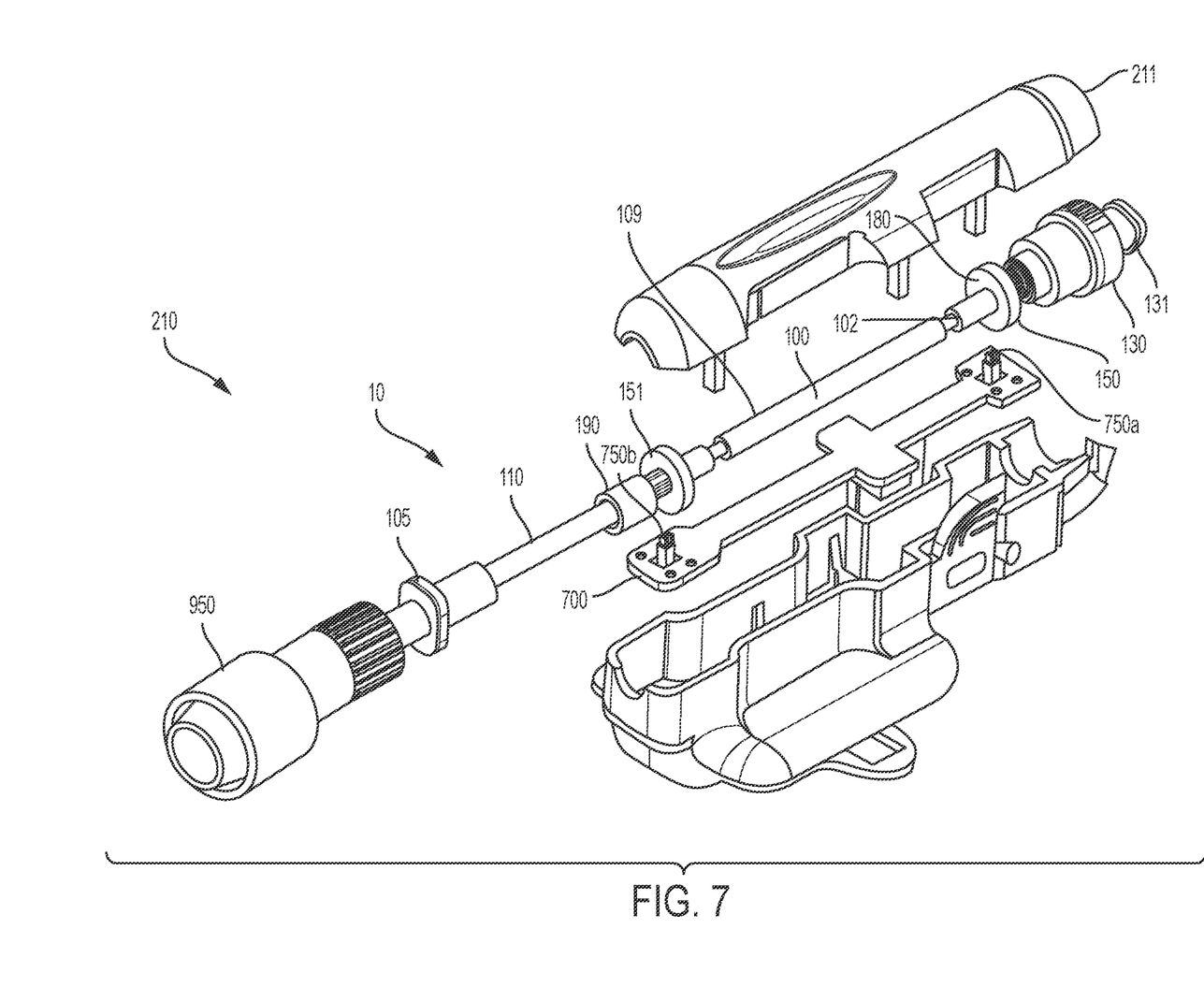
FIG. 7 is an exploded perspective view of a flow sensor system in accordance with one example of the present invention.

With reference to FIG. 7, instead of capping the outlet connection 105 with a cap 910, such as described herein with reference to FIG. 1, or a vented flow restrictor, such as a vented cap 940 described herein with reference to FIG. 2, the outlet connection 105 may be connected to a priming valve 950 as shown in FIG. 7. In some examples, the priming valve 950 is configured to interface with the Luer tip 109 of the outlet connection 105. The priming valve 950 can be attached to the Luer tip 109 by rotating the priming valve 950 about its longitudinal axis until the priming valve 950 stops, i.e., a secure connection between the priming valve 950 and the Luer tip 109 is made.

Once connected to the Luer tip 109, the priming valve 950, when closed, prevents fluid flow from the outlet connection 105 as described in more detail herein. The priming valve 950 is configured to open to allow fluid flow from the outlet connection 105 in response a threshold pressure within the flow sensor 210. For example, the outlet tubing 110 includes a fluid channel between a fluid inlet in fluid communication with the outlet end 101 of the flow tube 100 of flow sensor sub-assembly 10 and the outlet connection 105, and the priming valve 950 attached to the outlet connection 105 can be configured to open to allow the flow of the fluid from the outlet connection 105 in response a threshold pressure within the fluid channel of the outlet tubing 110.

Figure 8:
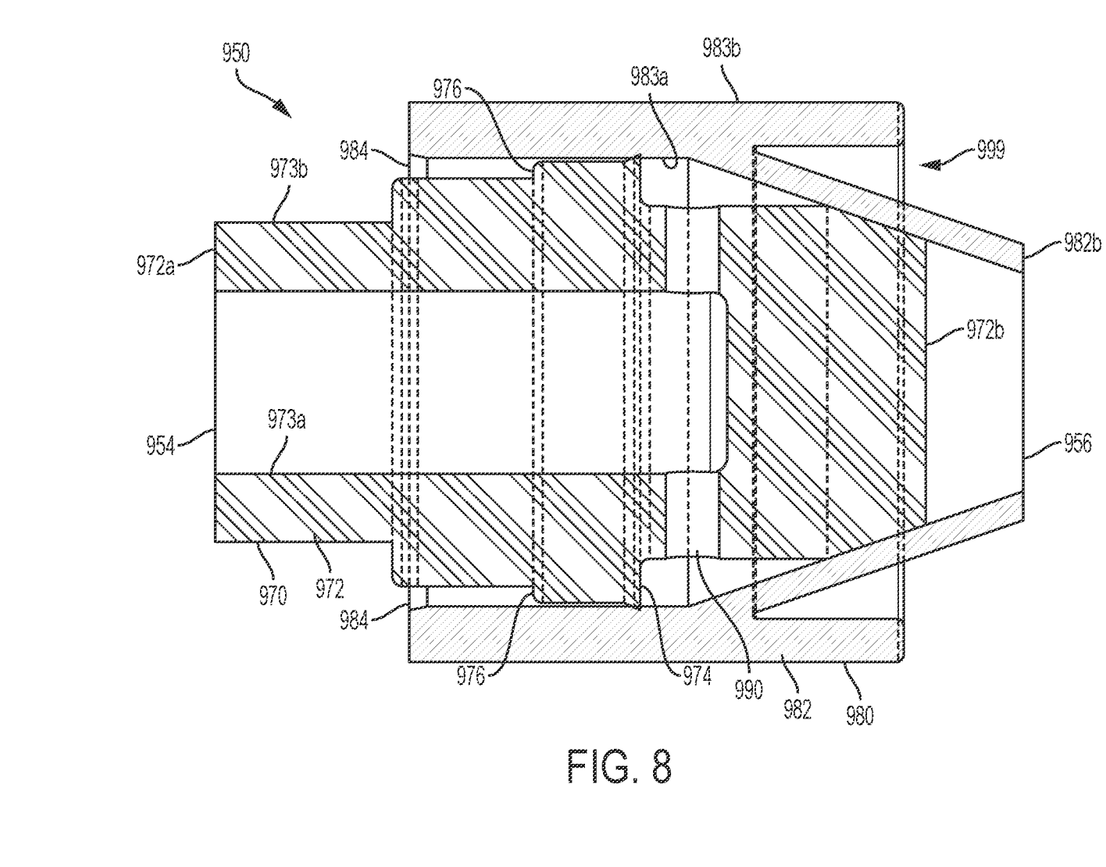
FIG. 8 is a schematic view of a priming valve in accordance with one example of the present invention.
Figure 9:
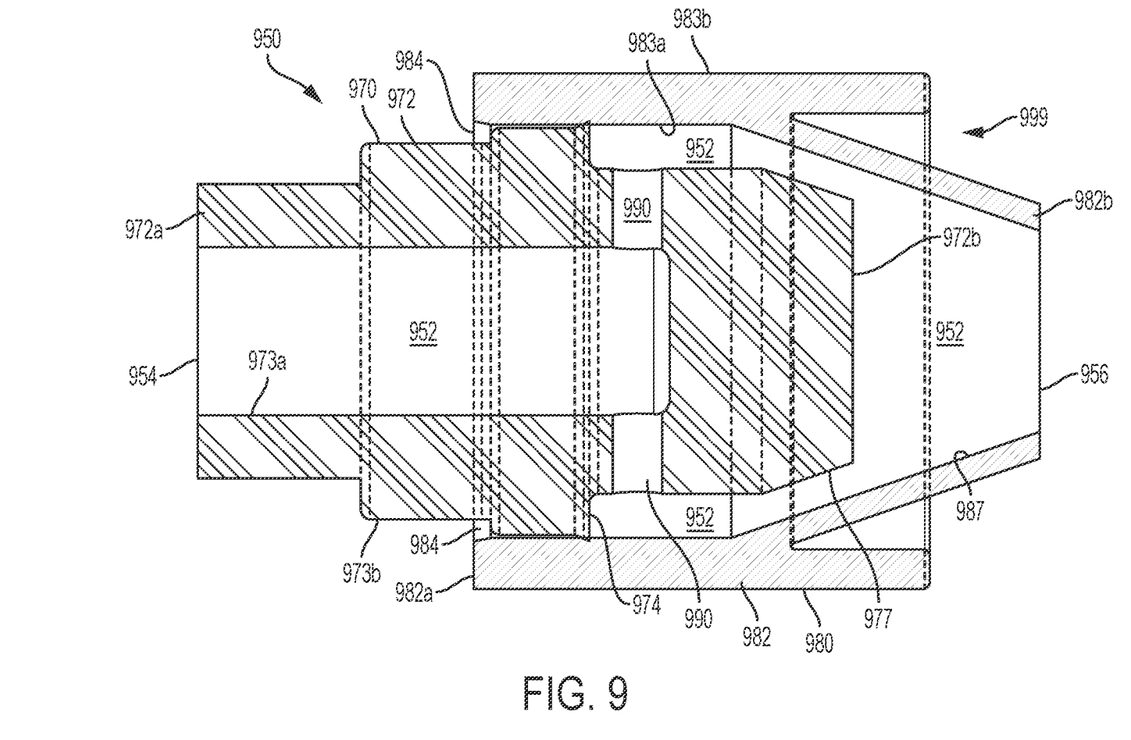
FIG. 9 is a schematic view of a priming valve in accordance with one example of the present invention.

Referring now to FIGS. 8 and 9, the priming valve 950 includes a fluid flow path 952, a fluid inlet 954 at a first end of the fluid flow path 952 configured to couple to the outlet connection 105, a fluid outlet 956 at a second end of the fluid flow path 952, a valve seat 970, and a connector 980 that engages the valve seat 970 to prevent fluid flow between the fluid inlet 954 and the fluid outlet 956 via the fluid flow path 952. The connector 980 is configured to move relative to the valve seat 970 in response to a threshold pressure within the fluid flow path 952 to allow fluid flow between the fluid inlet 954 and the fluid outlet 956 of the priming valve 950 via the fluid flow path 952. In some implementations, the threshold pressure can be 5-50 psi. For example, the connector 980 may be configured to remain engaged with the valve seat 970 until a pressure of 50 psi is present in the fluid flow path 952 that causes the connector 980 to move relative to the valve seat 970.

The valve seat 970 includes a sidewall 972 extending between an inlet end 972a and an outlet end 972b of the valve seat 970. The connector 980 includes a sidewall 982 extending between an inlet end 982a and an outlet end 982b of the connector 980. In some implementations, the sidewalls 972, 982 can be cylindrical sidewalls forming a cylindrically shaped valve seat 970 and a cylindrically shaped connector 980. At least a portion of the valve seat 970 extends within the connector 980, e.g., coaxially within the connector 980 as shown in FIGS. 8 and 9, such that an inner surface 983a of the sidewall 982 of the connector 980 faces an outer surface 973b of the sidewall 972 of the valve seat 970.

Figure 10:
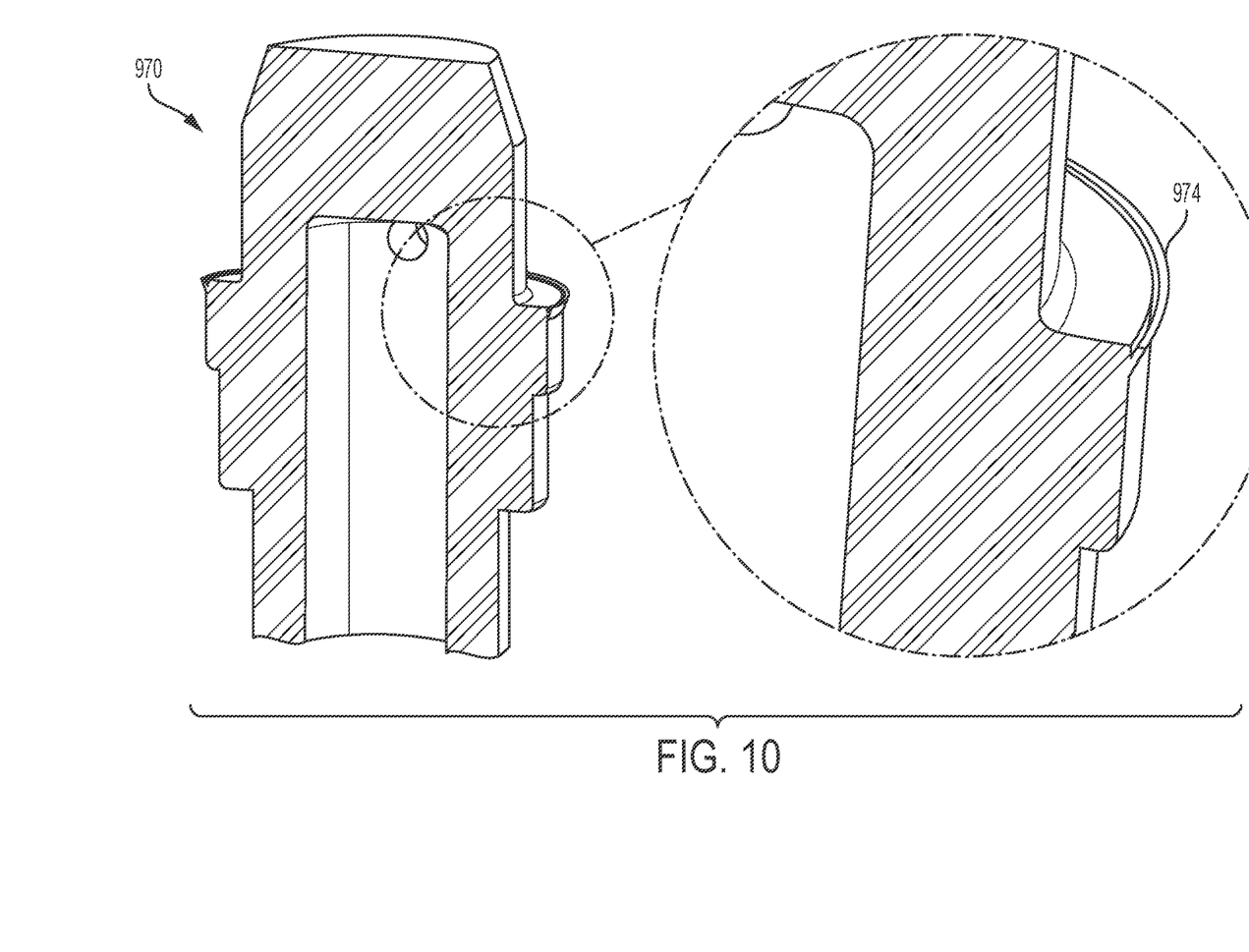
FIG. 10 is an exploded perspective view of a priming valve in accordance with one example of the present invention.

The outer surface 973b of the sidewall 972 of the valve seat 970 comprises a lip portion 974 that extends radially outward from the sidewall 972 of the valve seat 970. For example, a diameter of the valve seat 970 at the lip portion 974 is greater than a diameter of the remainder of the valve seat 970. The inner surface 983a of the sidewall 982 of the connector 980 is slidingly and sealingly engaged with the lip portion 974 of the valve seat 970. For example, the lip portion 974 of the valve seat 970 may include a molded lip seal, e.g., as shown in FIG. 10, or an o-ring configured to form a fluid tight seal with the inner surface 983a of the sidewall 982 of the connector 980 while still enabling the sidewall 982 of the connector 980 to slide along the lip portion 974.

An inner surface 973a of the sidewall 972 of the valve seat 970 defines a first portion of the fluid flow path 952 extending from the fluid inlet 954 of the priming valve 950 to at least one opening 990 in the sidewall 972 of the valve seat 970. The at least one opening 990 in the sidewall 972 of the valve seat 970 is located in a direction toward the fluid outlet 956 of the priming valve 950 with respect to the lip portion 974 of the valve seat 970. For example, as shown in FIGS. 8 and 9, two openings 990 are located on opposite sides of the sidewall 972 and to the right of the lip portion 974 towards the fluid outlet 956. Evenly spaced openings, such as the two openings 990 shown in FIGS. 8 and 9 enable the pressure in the fluid flow path to be more evenly distributed within the priming valve 970 and on the connector 980. The inner surface 983a of the sidewall 982 of the connector 980 and the outer surface 973b of the sidewall 972 of the valve seat 970 define a second portion of the fluid flow path 952 extending from the opening(s) 990 toward the fluid outlet 956 of the priming valve 950.

The connector 980 is configured to move axially away from the inlet end 972a of the valve seat 970 in a direction toward the outlet end 972b of the valve seat 970 in response to the threshold pressure within the fluid flow path 952 to allow the fluid to flow between the fluid inlet 954 and the fluid outlet 956 of the valve 950 via the fluid flow path 952.

In some examples, a portion of the sidewall 982 of the connector 980 can extend radially inward at the inlet end 982a of the connector 980. For example, as shown in FIGS. 8 and 9, retainer 984 can extend radially inward at the inlet end 982a of the connector 980. The retainer 984 extends radially inward farther than the lip portion 974 extends radially outward. The outer surface 973b of the sidewall 972 of the valve seat 970 comprises at least one abutment surface 976 that extends radially outward from the sidewall 972 of the valve seat 970. For example, a height of the lip portion 974 facing toward the fluid inlet 954 of the priming valve 950 can form the at least one abutment surface 976. The at least one abutment surface 976 is configured to engage the retainer 984 to inhibit further movement of the connector 980 axially away from the inlet end 972a of the valve seat 970 in the direction toward the outlet end 972b of the valve seat 970. For example, the connector 980 is enabled to move relative to the valve seat 970 a sufficient distance to open the fluid flow path 952 at the fluid outlet 956 of the priming valve 950 to a desired or predetermined width, (e.g., to achieve a desired flow rate based on the threshold pressure in the fluid flow path 952 and/or a flow rate and volume of a fluid delivered/to be delivered via the fluid flow path 952), after which the connector 980 is prevented from any further movement in that direction by the retainer 984 engaging the at least one abutment surface 956. The retainer 984 may be formed by applying heat and/or ultrasonic waves to the sidewall 982 of the connector 980 to extend the sidewall 982 radially inward.

Figure 11:
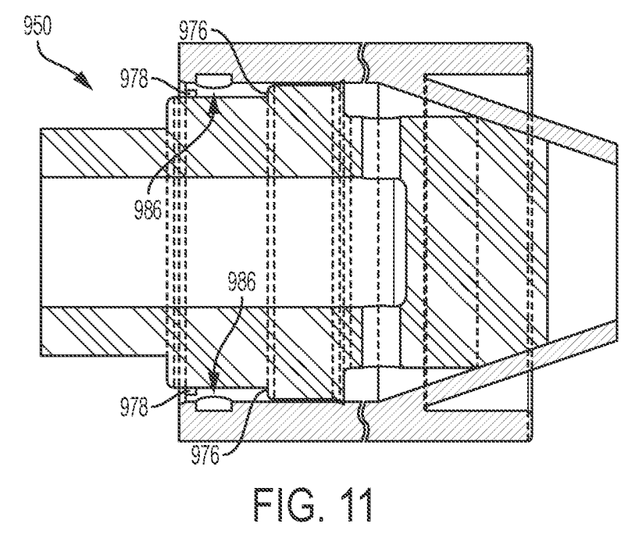
FIG. 11 is a schematic view of a priming valve in accordance with one example of the present invention.
Figure 12:
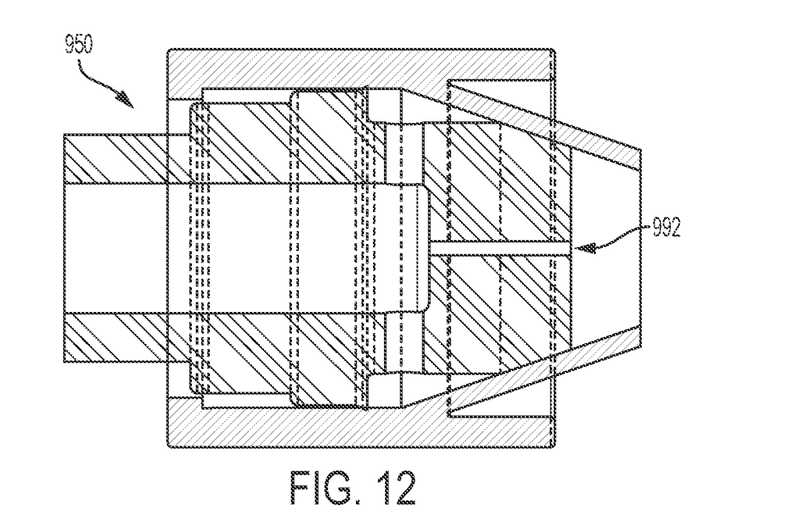
FIG. 12 is a schematic view of a priming valve in accordance with one example of the present invention.

In another example, as shown in FIG. 11, the inner surface 983a of the sidewall 982 of the connector 980 can include at least one detent 986 extending radially inward from the sidewall 982. The at least one detent 986 may be located at any position along the sidewall 982 between the inlet end 982a of the sidewall 982 and the lip portion 974 of the valve seat 970 when the priming valve 950 is in the closed position. The at least one abutment surface 976 is configured to engage the at least one detent 986 to inhibit further movement of the connector axially away from the inlet end 972a of the valve seat 970 in the direction toward the outlet end 972b of the valve seat 970. A location of the at least one detent 986 may be selected to enable the connector 980 to move relative to the valve seat 970 a sufficient distance to open the fluid flow path 952 at the fluid outlet 956 of the priming valve 950 to a desired or predetermined width, (e.g., to achieve a desired flow rate based on the threshold pressure in the fluid flow path 952 and/or a flow rate and volume of a fluid delivered/to be delivered via the fluid flow path 952), after which the connector 980 is prevented from any further movement in that direction by the at least one detent 986 engaging the at least one abutment surface 956.

In one implementation, the outer surface 973b of the sidewall 972 of the valve seat 970 may include at least one additional abutment surface 978 extending radially outward from the sidewall 972. The at least one additional abutment surface 978 is located in a direction toward the inlet end 972a of the valve seat 970 with respect to the at least one abutment surface 976. The at least one additional abutment surface 978 is configured to engage the at least one detent 986 to inhibit movement of the connector 980 axially toward the inlet end 972a of the valve seat 970 in a direction away from the outlet end 972a of the valve seat 970. The at least one detent 986 and the additional abutment surface 978 may be configured such that when a predetermined pressure or the threshold pressure is applied to the fluid flow path 952 the at least one detent can overcome the additional abutment surface 978, e.g., through deformation of the additional abutment surface 978, the detent 986, and/or the sidewall 982 of the connector 980, enabling further movement of the connector 980 axially away from the inlet end 972a of the valve seat 970 in the direction toward the outlet end 972b of the valve seat 970. After overcoming the additional abutment surface 978, engagement of an opposite face of the additional abutment surface 978 with the at least one detent 976 can act to inhibit the connector 980 from returning to the closed position by inhibiting movement of the connector axially toward the inlet end 972*a* of the valve seat 970 in the direction away from the outlet end 972*b* of the valve seat 970. It is noted that it can be beneficial to form the connector 980 as two separate pieces, e.g., as shown in FIG. 11, if detents 986 are included to retain the valve seat 970, with the two separate pieces being welded together after the valve seat 970 is assembled onto the inlet end 982*a* (left half in FIG. 11) of the connector.

In some examples, the priming valve 950 may include an additional fluid flow path 992 between the fluid inlet 954 and the fluid outlet 956 of the priming valve 950. The additional fluid flow path 992 can be sized and shaped to provide a visual indication of mist formation and/or to control back pressure within the fluid flow path 952. In some implementations, the additional fluid flow path 992 may be a needle having an inner diameter sufficiently small to be capable of generating back pressure in the flow sensor 210 when fluid is delivered from the syringe 900. For example, the additional fluid flow path 992 may be a needle having an outlet of approximately 30 G (0.16 mm ID). In other examples, the additional fluid flow path 992 may have an inner diameter of 0.1-0.2 mm. The priming fluid delivered from the syringe 900 builds back pressure within the flow sensor 210. In some examples, the increased fluid pressure of 5-50 psi within the flow sensor 210 can be maintained for a predetermined period of time. For example, the predetermined period of time may be approximately 1-60 seconds.

The inner surface 983*a* of the sidewall 982 of the connector 980 can include an angled surface 987 that extends radially inward toward the outlet end 982*b* of the connector 980 and beyond the outlet end 972*b* of the valve seat 970. The outer surface 973*b* of the sidewall 972 of the valve seat 970 includes a valve seat surface 977, and the angled surface 987 of the connector 980 can engage the valve seat surface 977 of the valve seat 970 to prevent fluid flow between the fluid inlet 954 and the fluid outlet 956 via the fluid flow path 952. The priming valve 950 may include a valve outlet connection 999 at the fluid outlet 954 at the second end of the fluid flow path 952 configured to connect to an inlet configured to deliver the fluid from the administrable fluid source to a fluid pathway that provides the fluid to a medical device. For example, the valve outlet connection 999 may be a Luer-Lok connection or Luer Slip connection.

Method of Readying a Flow Sensor System with a Relief Valve

The priming valve 950 can be used instead of the cap 910 or the vented cap 940 in use of a flow sensor system 200 of the present disclosure as described herein in the section titled "Method of Readying a Flow Sensor", accordingly its use therein is described only briefly below. For example, while the flow sensor 210 is pressurized by the fluid from the syringe 900, at least one first signal is generated by the flow sensor 210 to characterize at least one attribute of fluid. In various examples, the at least one attribute may be fluid flow rate and/or fluid pressure. The manual increase of fluid pressure within the flow sensor 210, while keeping the outlet connection 105 capped, helps eliminate any air between the interior surface of the flow path of the flow sensor 210 and the fluid. In this manner, the interior surface of the flow path of the flow sensor 210 is fully wetted to allow for an increased ultrasonic signal transmission of the flow sensor 210.

When the fluid pressure within the flow sensor 210 reaches the threshold pressure of the priming valve 950, which until this point has been closed to prevent fluid flow from the outlet connection 105, the priming valve opens to allow the flow of the fluid from the outlet connection 105. The priming valve is formed and configured such that the threshold pressure results in the interior surface of the flow path of the flow sensor 210 being fully wetted to allow for an increased ultrasonic signal transmission of the flow sensor 210 before the priming valve 950 opens to release the pressure. In some examples, the increased fluid pressure of 5-50 psi within the flow sensor 210 can be maintained for a predetermined period of time before the threshold pressure is reached. For example, the predetermined period of time may be approximately 1-60 seconds. The opening of the priming valve 950 can provide an indication to a medical practitioner that sufficient pressure within the flow sensor 210 has been achieved to ensure that the flow sensor 210 is fully wetted.

Next, the pressure on the plunger 920 of the syringe 900 can be released and the valve outlet connection 999 is attached to an inlet of a fluid pathway (not shown) configured for delivering fluid from an administrable fluid source, such as the syringe 900, to a patient. Alternatively, after the pressure on the plunger 920 of the syringe 900 is be released, and the priming valve 950 can be removed from the Luer tip 109, and the outlet connection 105 is attached to an inlet of a fluid pathway (not shown) configured for delivering fluid from an administrable fluid source, such as the syringe 900, to a patient. In some examples, the fluid pathway may be a catheter configured for connecting to a patient. Prior to connecting the fluid pathway to the patient, fluid from the syringe 900 is first expelled from the fluid pathway, such as during the priming of the fluid pathway, which can be performed with the priming valve still attached to the outlet connection 105, thereby providing an additional ease of use for medical practitioners. As the fluid is delivered from the syringe 900, the fluid flows through the flow sensor 210 and out of the fluid pathway. In some examples, 2-7 ml of fluid may be delivered from the syringe 900 through the fluid pathway. The flow sensor 210 may generate at least one second signal of the same type as the first signal in order to characterize at least one attribute of the fluid. For example, the second signal may characterize the pressure and/or flow rate of fluid through the flow sensor 210. In some examples, the second signal may be increased (i.e., have higher strength) than the first signal due to the internal surfaces of the flow path of the flow sensor 210 being fully wetted. For example, the second signal may be increased over the first signal by 120%, 160%, or 180%, inclusive of the values therebetween. The flow sensor 210 is now primed and ready for use in a fluid delivery procedure.

Method of Using the Flow Sensor System

To use a primed flow sensor system 200, a user attaches the flow sensor 210 to the base 220 by joining the flow sensor 210 (tubing side) and base 220 front sections first, and then snapping the two together. Preferably, an audible snapping sound is heard to indicate a secure connection between the flow sensor 210 and the base 220. In one example, connecting the flow sensor 210 to the base 220 automatically powers on the flow sensor system 200. In one example, the connection of the flow sensor 210 to the base 220 is verified by a blinking light on the base 220. In other examples, other indicators may be used.

The flow sensor system 200 is now ready for delivery of IV medications. In one example, in the event of a flow sensor system 200 failure (excluding the IV fluid pathway), the flow sensor system 200 will still allow standard medication or fluid delivery through the port.

Next, giving an injection using the flow sensor system 200 will be discussed. First, the injection port 130 is cleaned by swabbing the hub according to normal hospital procedure. Next, a syringe 900 can be attached to the injection port 130 of the flow sensor 210 by completely rotating the syringe 900 until the syringe 900 stops, i.e., a secure connection between the syringe 800 and the injection port 130 is made. Ideally, the caregiver double checks each medication name and concentration on the syringe 900 prior to attachment to the injection port 130 to assure the correct medication is given.

The flow sensor 210 can be disposed after the flow sensor 210 is used to sense the flow of at least one fluidic medicament. The flow sensor base 220 can be used with a plurality of different flow sensors 210.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as they become within known or customary practice in the art to which this disclosure pertains and which fall within the limits of the appended claims.

What is claimed is:

1. A method for readying a fluidic conduit associated with a medical device, the method comprising:

pressurizing a fluid in the fluidic conduit between a fluid inlet and a fluid outlet of the fluidic conduit at a predetermined pressure for a predetermined period of time to wet an interior surface of the fluidic conduit with the fluid, thereby removing air bubbles from the pressurized fluid in the fluidic conduit;

after the predetermined period of time, further pressurizing the fluid in the fluidic conduit between the fluid inlet and the fluid outlet of the fluidic conduit to achieve a threshold pressure in the fluidic conduit; and allowing the fluid to flow from the fluid outlet of the fluidic conduit in response to achieving the threshold pressure in the fluidic conduit.

2. The method of claim 1, further comprising:

delivering the fluid through the fluidic conduit; and generating a signal from a fluid sensor characterizing at least one attribute of the fluid.

3. The method of claim 2, wherein the at least one attribute of the fluid is fluid flow rate.

4. The method of claim 1, wherein the predetermined pressure is 5-50 psi.

5. The method of claim 1, wherein the predetermined period of time is 1-60 seconds.

6. The method of claim 2, wherein generation of the at least one signal is by providing fluid flow through the fluidic conduit.

7. The method of claim 2, wherein generation of the signal is by providing 2-7 ml of fluid flow through the channel.

8. The method of claim 2, wherein the fluid sensor is an ultrasonic fluid sensor.

* * * * *